United States Patent
Biard et al.

(10) Patent No.: US 6,639,083 B1
(45) Date of Patent: Oct. 28, 2003

(54) METHOD FOR PREPARING A THIOPENE DERIVATIVE

(75) Inventors: Michel Biard, Sisteron (FR); André Bousquet, Sisteron (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/111,159

(22) PCT Filed: Oct. 19, 2000

(86) PCT No.: PCT/FR00/02909

§ 371 (c)(1),
(2), (4) Date: Apr. 19, 2002

(87) PCT Pub. No.: WO01/29024

PCT Pub. Date: Apr. 26, 2001

(30) Foreign Application Priority Data

Oct. 22, 1999 (FR) .............................. 99 13205

(51) Int. Cl.⁷ ............................................. C07D 333/08
(52) U.S. Cl. ........................................................ 549/83
(58) Field of Search ............................................ 549/83

(56) References Cited

U.S. PATENT DOCUMENTS 4,127,580 A * 11/1978 Braye .......................... 546/114

FOREIGN PATENT DOCUMENTS

WO  WO 98 57974  12/1998

OTHER PUBLICATIONS

Kang et al., 1991, Tetrahedron, Elsevier Science Ltd, 55(14):4271–4286.*

Screttas, C.G.; "On the Mechanism of Ring Metallation of Aromatic Compounds. Metallation of Thiophen by Lithium and by Lithium Dihydroarylides"; Journal of the Chemical Society, Perkin Transactions 2, GB, Chemical Society; Letchworth, 1974, pp. 745–748.

Trifonov, A. et al; "Synthesis of asymmetric beta–hydroxy–cyclopentadienyl ligands and of their bidentate lanthanide complexes"; Journal of Organometallic Chemistry, CH, Elsevier–Sequoia S.A. Lausanne; vol. 452, No. 2, Jun. 20, 1999, pp. 211–217.

* cited by examiner

*Primary Examiner*—Joseph K. McKane
*Assistant Examiner*—Rei Tsang Shiao
(74) *Attorney, Agent, or Firm*—Paul E. Dupont; Michael D. Alexander

(57) ABSTRACT

The invention relates to a process for preparing 2-thienyl-2-ethanol, in which:
  a) thiophene is metallated using an alkali metal, in the presence of an electron transfer agent,
  b) the compound obtained is treated with ethylene oxide,
  c) the thienyl derivative thus formed is hydrolyzed, to give the desired compound.

2-Thienyl-2-ethanol is a synthetic intermediate.

16 Claims, No Drawings

METHOD FOR PREPARING A THIOPENE DERIVATIVE

This application is a 371 of PCT/FR00/02909 Oct. 19, 2000.

The present invention relates generally to a process for preparing a thiophene derivative.

More particularly, the invention relates to a process for preparing 2-thienyl-2-ethanol of formula:

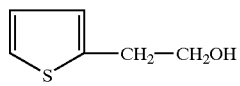

This compound has been found to be advantageous as a synthetic intermediate for preparing various chemical products, especially medicinal products derived from [3,2-c]thienopyridine, which are useful as platelet aggregation inhibitors and antithrombotic agents.

Among the [3,2-c]thienopyridine derivatives endowed with such properties, mention may be made in particular of 5-(2-chlorobenzyl)-4,5,6,7-tetrahydro[3,2-c]thienopyridine or ticlopidine (DCI) and also methyl α-(4,5,6,7-tetrahydro[3,2-c]thieno-5-pyridyl)(2-chlorophenyl)acetate, more particularly in the form of its dextrorotatory enantiomer, or clopidogrel.

Various processes for the industrial preparation of 2-thienyl-2-ethanol are known. One of the most widely used is without doubt the process described in U.S. Pat. No. 4,127,580 involving the metallation of thiophene using butyllithium, the treatment of the 2-lithiated derivative thus obtained with ethylene oxide and the hydrolysis of the compound formed to give the desired compound.

However, this process is not free of drawbacks on account, firstly, of the production of butane that is inherent to the use of butyllithium, and secondly the relatively high cost of this metallating agent, which proportionally represents a large fraction of the cost price of the [3,2-c]thienopyridine derivatives finally obtained.

The preparation of 2-thienyl-2-ethanol in an industrially viable process capable of avoiding the drawbacks of the above prior process remains of unquestionable interest.

Various examples of the metallation of thiophene starting with an alkali metal have been reported in the chemical literature.

For example, the preparation of 2-thienylcarboxylic acid by transient metallation of thiophene using the naphthalene-sodium complex, followed by carbonatation of the sodium derivative to obtain the acid in question, has been disclosed.

However, the yield of acid thus formed was only 40%. An entirely similar reaction was reported in J. Chem. Soc. Perkin II (1974), 745–748. However, in the described process, the sodium was replaced with lithium to give, after carbonatation, 41% of 2-thiophenecarboxylic acid.

However, this article mentions a modification to the lithiation process described, in which the thiophene is metallated with the lithium-naphthalene complex in the presence of 1,1-diphenylethylene or α-methylstyrene to give, after carbonatation, 2-thiophenecarboxylic acid in yields of at least 77% or even greater than 90%.

It has now been found, surprisingly, that 2-thienyl-2-ethanol can be obtained in very high yields of the order of 80% by intermediate sodation of thiophene using sodium and α-methylstyrene with the exclusion of naphthalene.

Thus, according to the invention, 2-thienyl-2-ethanol is prepared according to a process involving the following steps:

a) metallation of thiophene using an alkali metal, in the presence of an electron transfer agent, b) treatment of the compound thus obtained with ethylene oxide, c) hydrolysis of the thienyl derivative thus formed to give the desired 2-thienyl-2-ethanol.

The alkali metal used in the process of the invention may be lithium, sodium or potassium. However, sodium is a particularly preferred alkali metal.

This alkali metal is usually and preferably used in the form of a dispersion of the finely divided metal in a medium that is not electron-donating, the size of the sodium particles thus divided ranging from 1 to 100 microns, more generally from 1 to 30 microns and preferably from 1 to 10 microns.

Such sodium dispersions can be obtained by heating a mixture of sodium in a suitable medium to a temperature above 97.5° C., to give a binary system of immiscible liquids that may be emulsified in the same manner as water and oil. Subsequently, when this emulsion is cooled below this temperature of 97.5° C., the sodium solidifies in the form of minute spheroids in suspension in the medium under consideration.

Consequently, sodium dispersions can be prepared by heating a mixture of sodium metal in a suitable medium, to beyond the melting point of sodium, and by emulsifying the whole by very rapid stirring. The medium must have a boiling point higher than the melting point of the metal, unless the dispersion is prepared at a pressure above atmospheric pressure. In this case, it may be envisaged to use thiophene-both as the reagent and also as the medium for dispersing the sodium.

Generally, the dispersion medium under consideration consists of one or more aromatic or saturated liquid hydrocarbons such as, for example, toluene, a xylene or n-octane.

Toluene is a particularly advantageous dispersion medium. In order especially to avoid the aggregation of the metal and so as to reduce the surface tension, one or more dispersants may be added, if necessary, during the stirring phase when the metal is at a temperature above its melting point.

Alternatively, these dispersants can be introduced into the dispersion medium before or simultaneously with the addition of the metal.

Dispersants that are generally used include higher fatty acids preferably containing at least 15 carbon atoms, such as, for example, oleic acid, higher fatty alcohols or esters of high molecular weight, these compounds preferably containing at least 15 carbon atoms.

A polymer such as polyethylene, which will especially have the effect of greatly increasing the stability of the dispersion medium, may also be used.

These dispersants will usually be used in a proportion of from 0.5% to 1% of the weight of metal used.

Moreover, the metallation reaction is carried out in the absence of water and under an inert atmosphere generally at a temperature that may range from 0° C. to +40° C., for example at a temperature from 0° C. to +30° C. and preferably at a temperature from about 0° C. to +10° C.

This reaction advantageously takes place in a solvent, preferably an ether such as, for example, tetrahydrofuran or dimethoxyethane, and preferably in the presence of a slight excess of thiophene, such as from 1.2 to 1.5 mol per mole of metal.

In addition, this metallation reaction is carried out in the presence of an agent capable of transferring a single electron between the metal and the thiophene. These are generally aliphatic or aromatic conjugated diene compounds that may be selected from the compounds of formula:

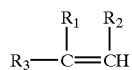

in which:

$R_1$ represents hydrogen or a methyl, ethyl or phenyl radical, $R_2$ represents hydrogen or a methyl or ethyl radical, $R_3$ represents a radical

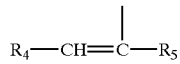

in which $R_4$ and $R_5$, which may be identical or different, represent hydrogen or a methyl or ethyl radical or $R_3$ represents a phenyl, benzyl or 1-phenyl-1-ethyl group.

Among the compounds of formula I above that may be mentioned are 1,3-butadiene, 2-methyl-1,3-butadiene or isoprene, 1-phenylethylene or styrene, 1-methyl-1-phenylethylene or α-methylstyrene, 1,1-phenylethylene, 2,3-dimethyl-1,3-butadiene, 1,3-pentadiene and 2,4-hexadiene.

Isoprene, α-methylstyrene and 2,3-dimethyl-1,3-butadiene represent single-electron-transfer agents that are particularly advantageous in the context of the invention. However, isoprene and better still α-methylstyrene represent preferred conjugated dienes.

As regards the reaction with ethylene oxide, this preferably takes place in the thiophene metallation medium and at a temperature ranging from 0° C. to room temperature, in particular at a temperature of about 20° C.

Likewise, similar operating conditions may be observed for the hydrolysis reaction.

The nonlimiting examples that follow illustrate the process of the invention.

EXAMPLE 1

2-Ethyl-2-ethanol a) Preparation of the Sodium Suspension 53 g (61 ml) of toluene, 0.0265 g of polyethylene and 26.5 g (1.15 mol) of sodium cut into pieces are placed in a 250 ml round-bottomed flask under nitrogen, equipped with a stirrer and a condenser. The mixture is heated to 102° C. and then stirred for 0.5 hour. The suspension is then cooled to a temperature of between 20° C. and 25° C.

b) Metallation of the Thiophene 145.4 g (133.7 ml; 1.731 mol) of thiophene are placed in a 1 l jacketed reactor under nitrogen, equipped with a dropping funnel and cooled with chilled dichloromethane. The mixture is cooled to 0° C.±1° C. with stirring.

The sodium suspension is then diluted, followed by addition to the thiophene. While keeping the temperature at 0° C.±1° C., this thiophene/sodium suspension is then added to a mixture of 51.8 g (76 ml; 0.762 mol) of isoprene in 166 g (187 ml; 2.3 mol) of tetrahydrofuran maintained at 0° C.±1° C. Under these conditions, the introduction time is about 1.5 h. The reaction is then maintained at 0° C.±1° C. for 2 hours.

c) Oxyethylenation 55.8 g (1.270 mol) of ethylene oxide are added to the mixture obtained in paragraph b) above, via a dip tube, while maintaining the temperature at 20° C.±1° C. The duration of this addition is about 1.5 h. The suspension is then stirred for 0.5 h at 20° C.±1° C.

d) Hydrolysis 300 ml of water and 74 g of ammonium chloride are placed in a 2 l reactor equipped with a cooling and stirring system.

This solution is cooled to a temperature of between −5° C. and 0° C. and the reaction mixture obtained in paragraph c) is then transferred, by nitrogen pressure, over 10 to 15 minutes, onto the ammonium chloride solution.

Under these conditions and with a cooling bath containing ice and methanol, the temperature at the end of hydrolysis is 20° C.

The mixture is stirred for 15 minutes at 20° C.±2° C., the phases are separated by settling for 15 minutes and the (upper) organic phase is washed 3 times at 20° C.±2° C. with 200 ml of water. The combined aqueous phases are extracted 3 times at 20° C.±2° C. using 100 ml (86 g) of toluene.

The organic phases are pooled and the toluene solution is concentrated under vacuum (50° C.; 15 mmHg).

In this way, 133 g of crude 2-thienyl-2-ethanol are obtained. Yield: 83%.

EXAMPLE 2

2-Ethyl-2-ethanol a) Preparation of the Sodium Suspension 69 g (80 ml) of toluene, 0.0230 g of oleic acid and 23 g (1 mol) of sodium cut into pieces are placed in a 250 ml round-bottomed flask under nitrogen, equipped with a stirrer and a condenser. The mixture is heated to 102° C. and then stirred for 0.5 hour. The suspension is then cooled to a temperature of between 20° C. and 25° C.

b) Metallation of the Thiophene 126 g (1.5 mol) of thiophene are placed in a 1 l jacketed reactor under nitrogen, equipped with a dropping funnel and cooled with chilled isopropanol. The mixture is cooled to 0° C.±1° C. with stirring.

The sodium suspension is then diluted, followed by addition to the thiophene. While keeping the temperature at 0° C.±1° C., this thiophene/sodium suspension (76 ml; 0.762 mol) is then added to a mixture of 79 g (0.670 mol) of α-methylstyrene in 144 g (2 mol) of tetrahydrofuran maintained at 0° C.±1° C. Under these conditions, the introduction time is about 1.5 h. The reaction medium is then maintained at 0° C.±1° C. for 2 hours.

c) Oxyethylenation 48 g (1.1 mol) of ethylene oxide are added to the mixture obtained in paragraph b) above, via a dip tube, while maintaining the temperature at 20° C.±1° C. The duration of this addition is about 1.5 h. The suspension is then stirred for 0.5 h at 20° C.±1° C.

d) Hydrolysis 230 ml of water are placed in a 2 l reactor equipped with a cooling and stirring system. This solution is cooled to a temperature of between 0° C. and 5° C. and the reaction medium obtained in paragraph c) is then transferred into the water, over 10 to 15 minutes. Under these conditions and with a cooling bath containing ice and methanol, the temperature at the end of hydrolysis is in the region of 20° C. The phases are separated by settling and the upper organic phase is concentrated under vacuum (50° C.; 15 mmHg).

In this manner, 239 g of crude 2-thienyl-2-ethanol are obtained. Yield: 83%.

EXAMPLE 3

Preparation of 2-thienyl-2-ethanol a) Preparation of the Sodium Suspension 84.3 g of dry toluene, 0.32 ml of oleic acid and 28.1 g (1.2217 mol) of sodium cut into pieces are placed into a 250 ml round-bottomed flask under nitrogen, equipped with a stirrer and a condenser. The mixture is heated to 102° C. and then stirred for 0.5 h.

The suspension is then cooled to a temperature in the region of 25° C.

b) Metallation of the Thiophene 154.2 g (1.5 equivalents) of thiophene are placed in a jacketed 1 l reactor under a nitrogen atmosphere, equipped with a dropping funnel and cooled. The flask is cooled to 0° C. with stirring and the sodium suspension is added to the thiophene. 67.2 g (0.67 equivalent) of 2,3-dimethyl-1,3-butadiene are added to 176 g (2 equivalents) of tetrahydrofuran, while keeping the temperature at 0° C.±1° C. The reaction medium is then maintained at 0° C. for 2 hours.

c) Oxyethylenation 59.2 g of ethylene oxide are added, via a dip tube, to the mixture obtained in paragraph b) above, while keeping the temperature below or equal to 20° C. The reaction medium is then left for 20 minutes at 20° C. with stirring.

d) Hydrolysis

The suspension obtained in paragraph c) is transferred, over 5 minutes and under a nitrogen pressure, into a 2 liter reactor containing 281 g of ice under nitrogen. The temperature of the medium at the end of introduction is 13° C. The mixture is stirred for 30 minutes and the phases are separated by settling. The organic phase is extracted with 100 ml of toluene, stirred for 30 minutes and the phases are separated by settling. The organic phase is then concentrated under vacuum.

In this way, 145.6 g of 2-thienyl-2-ethanol are obtained. Yield: 83%.

What is claimed is:

1. A process for preparing 2-thienyl-2-ethanol, wherein:
   a) thiophene is metallated using a dispersion of a finely divided alkali metal in a medium that is not electron-donating, in the presence of an electron transfer agent,
   b) the compound obtained is treated with ethylene oxide,
   c) the thienyl compound thus formed is hydrolyzed, to give the desired compound.

2. A process according to claim 1, wherein the alkali metal is sodium.

3. A process according to claim 2 wherein the sodium is in the form of particles ranging from 1 to 100 microns.

4. A process according to claim 3, wherein the sodium is in the form of particles ranging from 1 to 30 microns.

5. A process according to claim 2 wherein the medium that is not electron-donating is an aromatic or saturated liquid hydrocarbon.

6. A process according to claim 5 wherein the medium that is not electron-donating contains one or more dispersants.

7. A process according to claim 6, wherein the dispersant is used in a proportion of from 0.5% to 1% by weight of sodium.

8. A process according to claim 5 wherein the metallation is carried out in the presence of an electron transfer agent comprising a conjugated diene of formula:

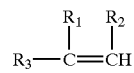

wherein:
   $R_1$ represents hydrogen or a methyl, ethyl or phenyl radical,
   $R_2$ represents hydrogen or a methyl or ethyl radical,
   $R_3$ represents a radical $R_4$—CH=C—$R_5$ in which $R_4$ and $R_5$, which may be identical or different, represent hydrogen or a methyl or ethyl radical or $R_3$ represents a phenyl, benzyl or 1-phenyl-1-ethyl group,
   at a temperature of from 0° C. to 40° C.

9. A process according to claim 8, wherein the conjugated diene is 1,3-butadiene, 2-methyl-1,3-butadiene, 1-phenylethylene, 1-methyl-1-phenylethylene, 1,1-phenylethylene, 1,3-pentadiene or 2,4-hexadiene.

10. A process according to claim 9 wherein the conjugated diene is 2-methyl-1,3-butadiene or 1-methyl-1-phenylethylene.

11. A process according to claim 1 wherein the metallation is carried out at a temperature of from 0° C. to 40° C.

12. A process according to claim 1 wherein the treatment with ethylene oxide and the hydrolysis are carried out at a temperature from 0° C. to room temperature.

13. A process according to claim 4 wherein the sodium is in the form of particles ranging from 1 to 10 microns.

14. A process according to claim 10 wherein the metallation is carried out at a temperature of from 0° C. to 40° C.

15. A process according to claim 10 wherein the treatment with ethylene oxide and the hydrolysis are carried out at a temperature from 0° C. to room temperature.

16. A process according to claim 14 wherein the treatment with ethylene oxide and the hydrolysis are carried out at a temperature from 0° C. to room temperature.

* * * * *